(12) United States Patent
Ptock et al.

(10) Patent No.: US 6,881,854 B2
(45) Date of Patent: Apr. 19, 2005

(54) CONJUGATED UNSATURATED GLYCERIDE MIXTURES AND A METHOD FOR PRODUCING THE SAME

(75) Inventors: Arne Ptock, Ludwigshafen (DE); Kai-Uwe Baldenius, Ludwigshafen (DE); Andreas Keller, Germersheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/473,217

(22) PCT Filed: Mar. 26, 2002

(86) PCT No.: PCT/EP02/03354

§ 371 (c)(1),
(2), (4) Date: Sep. 29, 2003

(87) PCT Pub. No.: WO02/079139

PCT Pub. Date: Oct. 10, 2002

(65) Prior Publication Data

US 2004/0116738 A1 Jun. 17, 2004

(30) Foreign Application Priority Data

Mar. 29, 2001 (DE) .......................................... 101 15701

(51) Int. Cl.⁷ .............................................. C07C 57/00
(52) U.S. Cl. ....................... 554/221; 554/126; 554/224; 554/227; 514/560; 426/601
(58) Field of Search ................................ 554/221, 224, 554/227, 12.5; 420/601; 574/560

(56) References Cited

U.S. PATENT DOCUMENTS

| | | |
|---|---|---|
| 3,162,658 A | 12/1964 | Baltes et al. |
| 6,177,580 B1 | 1/2001 | Timmermann et al. |
| 6,225,486 B1 * | 5/2001 | Saebo et al. ................. 554/221 |

FOREIGN PATENT DOCUMENTS

| | | |
|---|---|---|
| BR | 8202429 | 4/1982 |
| DE | 1 156788 | 12/1959 |
| DE | 1 156789 | 11/1963 |
| DE | 25 17 377 | 10/1976 |
| EP | 779 033 | 6/1997 |
| EP | 839 897 | 5/1998 |
| EP | 799 033 | 9/2001 |
| GB | 925 148 | 5/1963 |
| WO | 94/16690 | 8/1994 |
| WO | 96/06605 | 3/1996 |
| WO | 97/32008 | 9/1997 |
| WO | 97/46118 | 12/1997 |
| WO | 97/46230 | 12/1997 |
| WO | 99/29317 | 6/1999 |
| WO | 01/17374 | 3/2001 |
| WO | 01/18161 | 3/2001 |

OTHER PUBLICATIONS

Zh.Org.Khim.18 (1982) 11, 2261–66.
XP–002211856, Bajgrowicz et al.,7461–7472.
XP–002211857, Eskola et al., Am.Chem.Soc.1997,62, 5732–5742.
J.Food Comp. and Analysis 5, 185–197 (1992) Chin et al.
Banni et al., Carcinogenesis,vol. 20, 1999, 1019–1024.
Thompson,Cancer,Res.,vol. 57,1997, 5067–5072.
Cancer Res.,vol. 57,1997, 6118–6124, IP et al.
Farben,Lacke, Anstrichstoffe 4(1950) 149–159, Mikusch.
McNeill,J.Am.OilChem.Soc. 76(1999) 1265–1269.
Garcia et al.,Tech.12(1999) 369–373.
Garcia et al.,J Dairy Sci.2000, 83, 371–377.
Garcia ,Biotechnology Lts. (1998) 20, 393–395.
Houben Weyl, Bd. 5, S. 63ff.
J.Braz.Chem.Soc.vol. 9, No. 3, 199–210,1998.
J.Mol.Catal.A, Chemical 109 (1996) 37–44.
Chima 39 (1985) N4. 9, 269–272.
Cyclohexylguanidin in Zeolite Y; THL, vol. 38,No. 8, 1325–1328, 1997, Sercheli et al.
J.Mol.Catal.A, Chemical 109(1996) 37–44,Schuchardt et al.
MacDonald,J.J.Am.College of Nutrition (2000) 19, 111S–118S.
Schuchardt et al., J.Braz.Chem.Soc., vol. 9, No. 3, 199–201, 1998.

* cited by examiner

*Primary Examiner*—Deborah D. Carr
(74) *Attorney, Agent, or Firm*—Novak Druce & Quigg, LLP

(57) ABSTRACT

The invention relates to a process for conjugating two double bonds separated by a methylene bridge in a long-chain alkene, in which the long-chain alkene is isomerized with an
  a) imino base, or
  b) iminophosphorane base,
as catalyst.

29 Claims, No Drawings

CONJUGATED UNSATURATED GLYCERIDE MIXTURES AND A METHOD FOR PRODUCING THE SAME

The present invention relates to processes for preparing conjugated alkenes, in particular esterified fatty acids. The inventive process can preferably be used to prepare glycerides of conjugated fatty acids from synthetic or natural glyceride oils or fats or derivatives thereof. The present invention further relates to glyceride mixtures obtainable by the inventive process and to preparations which comprise the inventive glyceride mixtures. The invention further relates to processes for preparing the inventive preparations, processes for preparing drugs and kits which comprise the inventive preparations and/or glyceride mixtures.

TECHNICAL FIELD

Fatty acids and triglycerides have a multiplicity of applications in the food industry, animal nutrition, cosmetics and in the pharmaceutical sector. Depending on whether these are free saturated or unsaturated fatty acids, or triglycerides having an elevated content of saturated or unsaturated fatty acids, they are suitable for the most widespread applications. Thus, for example, a high content of lipids having unsaturated fatty acids and, especially, polyunsaturated fatty acids, is important for the nutrition of animals and humans, since these, for example, have a beneficial effect on the triglyceride level or cholesterol level and thus decrease the risk of a heart disorder. Unsaturated fatty acids are used in various dietetic foods or drugs.

Particularly valuable and sought-after unsaturated fatty acids are the conjugated unsaturated fatty acids, for example conjugated linoleic acid (CLA). Conjugated polyunsaturated fatty acids are somewhat rare compared with other polyunsaturated fatty acids.

CLA is a collective term for positional and structural isomers of linoleic acid that are characterized by a conjugated double bond system starting at carbon 7, 8, 9, 10 or 11. Geometric isomers exist for each of these positional isomers, that is cis-cis, trans-cis, cis-trans, trans-trans.

C18:2 cis-9, trans-11 and C18:2 trans-10, cis-12 CLAs which are the isomers with the highest biological activity are especially of particular interest, since in animal experiments they have proved to be cancer-preventive, to have antiarteriosclerotic activity and, in humans and animals, to reduce the body fat content. Commercially, CLAs are currently principally marketed as the free fatty acid.

For humans, the most important natural sources of CLA are especially animal fats. Thus fats of ruminant animals such as cattle (Chin, Journal of Food Composition and Analysis, 5, 1992: 185–197) and sheep, and also dairy products, have very high CLA concentrations. In cattle from 2.9 to 8.9 mg of CLA/g of fat are found. In contrast, vegetable oils, margarines and fats from nonruminant animals have CLA concentrations of from only 0.6 to 0.9 mg/g of fat.

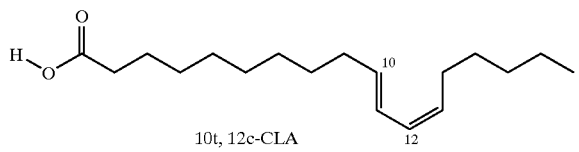

10t, 12c-CLA

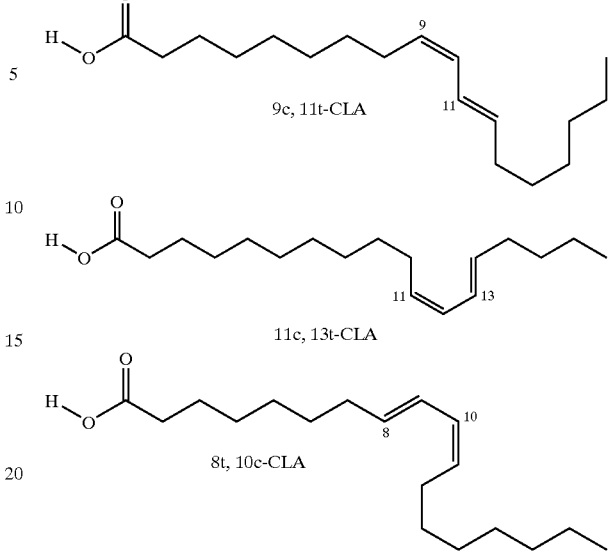

9c, 11t-CLA 11c, 13t-CLA 8t, 10c-CLA

BACKGROUND ART

A number of beneficial-effects have been detected for CLA. Thus, the administration of conjugated linoleic acid decreases the body fat in humans and animals and improves the feed utilization in animals (WO 94/16690, WO 96/06605, WO 97/46230, WO 97/46118). By administering conjugated linoleic acid, for example, allergies (WO 97/32008), diabetes (WO 99/29317) or cancer (Banni, Carcinogenesis, Vol. 20, 1999: 1019–1024, Thompson, Cancer, Res., Vol. 57, 1997: 5067–5072) may also be beneficially affected. Polyunsaturated fatty acids are also added to infant food to "increase the nutritional value" and as essential building blocks which ensure growth and brain development.

Since CLA only occurs naturally in significant quantities in ruminants and their products, such as milk, cheese, etc., there is a great need for alternatives to CLA originating from these animal sources, in order to ensure balanced and healthy nutrition, in particular if the supply with animal fats is reduced, inadequate or if synthetic preparation is too expensive. Commercially, CLAs are currently principally marketed as free fatty acid. Free fatty acids such as CLA, however, generally do not occur naturally as free fatty acids, but are esterified to form biologically active triglycerides. In addition free fatty acids frequently possess disadvantageous sensory properties. For incorporation into foods, for example, triglycerides are also preferred to free fatty acids for technological reasons.

The processes described in the prior art generally consist of two or three process steps in which free fatty acids or their alkyl esters are first prepared and isomerized in order then to transesterify these with glycerol or glycerides under enzymatic or chemical catalysis to form triglycerides.

In the conventional preparation method for free CLA acids, unconjugated linoleic-acid-containing oils (for example sunflower seed oil, soybean oil or safflower oil) are isomerized, for example, with NaOH or KOH in ethylene glycol at 180° C. (Ip C. et al., Cancer Res. 51 (1991) 6118–6124). This process requires superstoichiometric amounts of alkali (based on fatty acids present in the oil) and produces substantial amounts of unwanted CLA isomers (in particular 8t, 10c- and 11c, 13t-CLA).

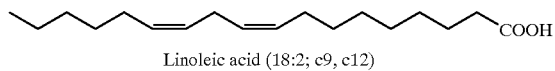

Linoleic acid (18:2; c9, c12)

EP-839897 describes a process in which, for the isomerization, linoleic acid-containing oils are reacted with KOH in propylene glycol at 150° C. Free CLA acids are obtained which contain only relatively small amounts of unwanted isomers. This process requires superstoichiometric amounts of KOH and corresponding amounts of mineral acids.

In one process, linoleic acid alkyl esters-are isomerized with catalytic amounts (0.3 to 1%) of potassium alkoxide, with CLA alkyl esters being obtained (DE-1156788 and DE-1156789).

To prepare triglycerides, in EP-0779033, linoleic acid is isomerized at 180° C. with NaOH in ethylene glycol to form free CLA and the free CLA is transesterified with palm oil triglycerides using immobilized *Mucor miehei* lipase. The triglyceride obtained as product contains approximately 8% of each of the two wanted CLA isomers (9c, 11t- and 10t, 12c-) in esterified form.

In some non-enzymatic processes, the esterification of glycerol and the transesterification of natural fats and oils with free CLA acids is carried out with the addition of known esterification catalysts at high temperatures (from 180 to 240° C.) (Mikusch; Farben, Lacke, Anstrichstoffe 4 (1950) 149–159; DE-19718245). The resultant CLA-containing triglycerides, owing to the temperature stress necessary in the process, have a high content of isomers which are unwanted for nutritional uses (in particular 8t,10c- and 11c,13t-CLA fatty acid radicals).

WO 01/18161 describes a solvent-free synthetic process for preparing CLA. The preparation of CLA from oil by alkali isomerization is also described there.

The individual CLA isomers can also be transesterified with the palm oil triglycerides after enrichment of the isomers. In this manner a CLA content of 30% in the triglyceride can be achieved. (McNeill, J. Am. Oil Chem. Soc. 76 (1999) 1265). The transesterification of butter fat with free CLA is based on a similar process, inter alia, immobilized *Candida antarctica* lipase acting as preferred catalyst (Garcia, Biotechnol. Tech. 12 (1999) 369–373; Garcia, J Dairy Sci 2000, 83:371–377; Garcia, Biotechnology Letters (1998) 20:393–395). In a similar manner, corn oil was also modified using chemically synthesized CLAs using lipase catalysis (Martinez, Food Biotechnology 1999, 13:183–193).

Processes described in the prior art which start from CLAs in the form of free fatty acids for preparing the triglycerides thus, using stoichiometric amounts of bases, release the fatty acids from oils containing non-conjugated polyunsaturated fatty acids and simultaneously carry out the conjugation. In the second process step, conjugated polyunsaturated fatty acids are reacted with glycerol or glycerides to form glycerides containing conjugated, polyunsaturated fatty acids.

Furthermore, in the prior art, in the preparation of glycerides containing conjugated, polyunsaturated fatty acids from glycerides or glycerol by reaction with alkyl esters of conjugated polyunsaturated fatty acids, the alkyl esters of conjugated, polyunsaturated fatty acids are obtained by transesterifying non-conjugated, polyunsaturated fatty acid-containing oils using catalytic amounts of alkali metal bases and superstoichiometric amounts of alcohols to give the alkyl esters of polyunsaturated fatty acids and these are then converted into the alkyl esters of conjugated fatty acids in a second process step using catalytic amounts of alkaline earth metal bases.

The processes described in the prior art thus have the disadvantage that two to three process steps are required, which is an economic disadvantage, to prepare glycerides containing conjugated, polyunsaturated fatty acids.

DISCLOSURE OF INVENTION

It is an object of the present invention thus to provide a rapid and economically advantageous process for producing conjugated double bonds in alkenes, in particular in esterified fatty acids, such as are present in triglycerides.

We have found that this object is achieved by the embodiments underlying the present invention.

The present invention therefore relates to a process for preparing a compound of the formula (III)

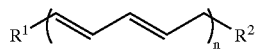

from a compound of the formula II

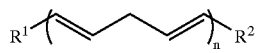

which comprises reacting the compound of the formula IV with an a) imino base, or
b) iminophosphorane base;

where n=1, 2, 3; and where
$R^1$ and $R^2$, or $R^1$ or $R^2$, can be:

H;

unbranched or branched $C_1$–$C_{10}$-alkyl,
  where 0, 1, 2 or 3 carbons can be replaced by epoxide, O, S,
  NZ, and/or —$X^1$—(C=$X^2$)—,
  where $X^1$ is a bond, O, S or NZ,
  and/or $X^2$ is O, S or NZ;

mono-, bi-, or tricyclic aromatic saturated or partially unsaturated $C_0$–$C_6$-alkyl carbocycle or heterocycle having from 3 to 6 carbons,
  where from 0 to 3 heteroatoms can be selected from the group consisting of S, N, and/or O;

and where each carbon of the alkyl chains or of the ring can bear 1, 2 or 3 of the following substituents OZ, SZ, (C=O )—OZ, NZZ$^1$, $C_1$ to $C_6$-alkyl, F, Br, Cl, I;

and where Z and/or $Z^1$ can be H or $C_1$–$C_6$-alkyl.

Particularly preferably, $R^1$ or $R^2$ independently of one another is H or an unbranched or branched $C_1$–$C_{10}$-alkyl, where each carbon of the alkyl chains or of the ring can bear up to three of the following substituents OZ, SZ, (C=O)—OZ, NZZ$^1$, $C_1$ to $C_6$-alkyl, F, Br, Cl, I, and where Z and/or $Z^1$ can be H or $C_1$–$C_6$-alkyl.

Preferably, the compound IV is a substituted or unsubstituted unbranched alkene having from 8 to 24 carbons as described below.

More preferably, the alkyl chain bears one of the following substituents OZ, SZ, (C=O)—OZ and Z and $Z^1$ as above, particularly preferably in a terminal position.

Preferably, compound IV is a C8 to C24 fatty acid, with esterified fatty acids being particularly preferred.

The invention consequently also relates to a process for conjugating two double bonds separated by a methylene bridge in a long-chain alkene, in which the long-chain alkene is isomerized with an a) imino base, or
b) iminophosphorane base, as catalyst.

A "long-chain" alkene according to the invention is an unbranched unsaturated carbon chain of at least six carbons. Preferably the invention relates to alkenes which contain from 8 to 24, more preferably from 10 to 24, preferentially from 12 to 22, even more preferably from 16 to 20 carbons. The double bonds of the long-chain alkene are separated from one another by a methylene bond (homoconjugated). The alkene can also contain more than one double bond, provided that it comprises one homoconjugated double bond. The term "alkene" also comprises derivatives of the alkene. Thus the alkene can be bound to other groups. Examples of such groups are described below for compound I as R. These can be bound terminally to the alkene, for example.

An "imino base" is a base that has an =NR— group of atoms (imino group) and preferably an additional proton donor, for example the —PH—, or preferably —NH—, group of atoms, in particular iminoamino bases. A "phosphorane" is an organophosphorus compound that has a valency of 5. An "iminophosphorane" additionally has an imino group, an "aminoiminophosphorane" additionally has up to three amino groups and one imino group and is also included. In particular triamino(imino)phosphoranes are included.

In the prior art, the isomerization of non-conjugated, polyunsaturated free fatty acids or their alkyl esters is described using basic compounds, such as alkoxides, alkalis, sodium amide or amines.

Houben Weyl, volume 5, pp. 63 ff. DE 25 17 377 describes the isomerization of 2,5-heptadienoic esters to their 3,5 derivatives using strongly basic amines, for example primary, secondary or tertiary amines, or quaternary ammonium bases, at temperatures from 20° C. to 90° C. Zakharkin, 1982, describes the isomerization of the methyl ester of 2Z,5E-heptadienoic acid to give the methyl ester of 3E,5E-heptadienoic acid, and of the 2E,5Z- and 2Z,5Z-ester mixture to give the methyl ester of 3E,5Z-heptadienoic acid (Zh. Org. Khim. 18 (1982) 11, 2261–66); in this process catalytic amounts of triethylamine are used to isomerize the double bond which is conjugated directly to the methyl ester. The use of the imino base guanidine and aminophosphorane bases to transesterify fatty acids in vegetable oils using protic alkyl alcohols, in particular methanol, to give their fatty alkyl esters is described by Schuchardt (J. Braz. Chem. Soc. Vol. 9, No. 3, 199–210, 1998; BR8202429).

The present invention is based on the surprising finding that polyunsaturated, non-conjugated double bonds, in particular in esterified fatty acids, can be isomerized to form conjugated double bonds using catalytic amounts of certain very strong bases, that is to say imino bases or iminophosphorane bases, in particular aminoimino bases or aminoiminophosphorane bases. The use of amines, in particular also triamines, as has been described in the prior art, did not lead to an isomerization of homoconjugated double bonds to form conjugated double bonds in the esters of fatty acids studied according to the inventive process. The examples tabulate by way of example which amines were used as catalysts for the inventive process.

Possibly, in the prior art, the double bond isomerized by triethylamine is activated by the adjacent carbonyl group. Preferably, therefore, none of the double bonds to be isomerized is activated. The term "non-activated double bond" here is taken to mean that the double bonds of the long-chain alkene to be conjugated are separated from an activating group by at least one methylene bridge. An activating group is taken to mean a group of atoms that facilitates substitution of the adjacent double bond compared with a non-adjacent double bond. The long-chain alkyl can bear no activating groups, or one or more activating groups; preference is given to a terminal activating group, the activating groups being localized in such a manner that the double bond to be isomerized is not activated. An activating group in particular has a high electronegativity. Activating groups can be, for example: —COOH, —COO—, —OH, —SO$_4$, —SO$_3$—, —CN—, =NR—, or halogen (F, Br, Cl, I). Most preferably, the activating group is an alkyl ester. Preferred alkyl esters are described below. In a preferred embodiment compound IV is therefore a fatty acid ester as described below.

The present invention therefore relates to a process for preparing a conjugated unsaturated fatty acid ester (FAE I), wherein a polyunsaturated fatty acid ester (FAE II) is isomerized using an imino base or iminophosphorane base as catalyst, in particular using an aminoimino base or aminoiminophosphorane base. The inventive process can be used, in particular, to convert alkyl esters of non-conjugated polyunsaturated fatty acids into their conjugated form.

A "fatty acid" is preferably an unbranched carboxylic acid having an even number of carbons (n) (e.g. in n=16). Preferably the invention relates to fatty acids having from 8 to 24, more preferably from 12 to 22, even more preferably from 16 to 22 carbons, particularly preferably from 18 to 22 carbons, very particularly preferably having 18 carbons.

A "polyunsaturated fatty acid" is a fatty acid having at least two double bonds, which can be conjugated or non-conjugated. If not specified otherwise, "polyunsaturated fatty acid" generally refers to fatty acids containing non-conjugated double bonds. A "conjugated, unsaturated fatty acid" is an unsaturated fatty acid having at least two double bonds that are conjugated. The non-conjugated, polyunsaturated fatty acid has two double bonds which are at positions n and n+3 (that is to say are homoconjugated), for example in the case of linoleic acid or linolenic acid, where n is a carbon of the carboxylic acid (see above).

MODE(S) FOR CARRYING OUT THE INVENTION

In an embodiment of the inventive process, the compound IV is present as esterified fatty acid (FA II), in particular as an alkyl ester.

An "alkyl ester" of the fatty acids is an ester thereof with alkanols, preferably with $C_1$- to $C_5$-alkanols, for example methanol, ethanol, propanol, isopropanol, n-butanol, isobutanol tert-butanol, or n-pentanol and its isomers (2-pentanol, 3-pentanol, 2-hydroxy-3-methylbutane). Particular preference is given to methanol and ethanol.

An "alkyl ester" of a fatty acid is also an organic compound so that said alkanols can be bound to other carbons or heteroatoms, for example H, O, S, P, halogens. Also included are bonds to aromatic and cyclic organic compounds and the derivatives enumerated below. Preference is given to alkyl esters which can be isomerized to form conjugated polyunsaturated fatty acids, for example to form conjugated linoleic acids (CLAs), α-parinaric acid (18:4 octadecatetraenoic acid), eleostearic acid (18:3 octadecatrienoic acid), dimorphecolic acid, conjugated linolenic acids and calendic acid, with particular preference given to CLA preparations which comprise 9cis,11trans-CLA alkyl esters and 10trans,12cis-CLA alkyl esters as product.

In a preferred embodiment of the inventive process, the compound IV or the esterified fatty acid (FA II) is present as a glyceride.

Surprisingly, it has been found that by means of the inventive process isomerization of polyunsaturated fatty acids, for example linoleic acid, that are esterified with a glyceride, in particular including with a triglyceride, it is possible to give conjugated unsaturated fatty acids contained in a glyceride, without releasing the fatty acids. A single-stage isomerization of polyunsaturated free fatty acids which are present bound in a glyceride with catalysis by imino bases or iminophosphorane bases, in particular aminoimino bases or aminoiminophosphorane bases is not described in the prior art. To date no economic process has been known for preparing glycerides containing conjugated polyunsaturated fatty acids in one stage with quantitative conversion from glycerides containing non-conjugated, polyunsaturated fatty acids. The inventive process, in contrast to the prior art, can start directly from the oils or fats containing non-conjugated, polyunsaturated fatty acids and avoids chemical derivatization to give the free fatty acids or their alkyl esters. The inventive process thus makes possible direct conjugation of non-conjugated polyunsaturated fatty acids directly in the glyceride.

A "glyceride" is glycerol esterified with one, two or three carboxylic acid radicals (mono-, di- or triglyceride). "Glyceride" is also taken to mean a mixture of different glycerides. Glyceride or the glyceride mixture can comprise other additives, for example free fatty acids, antioxidants, proteins, carbohydrates, vitamins and other substances, as are enumerated, for example, below under "additives".

The glyceride used in the inventive process can also be present in a synthetic or naturally occurring glyceride oil or a derivative or mixtures thereof. "Glyceride" can also be taken to mean, depending on the context, synthetic or naturally occurring fatty acid esters and/or oils and fats comprising glycerides, also referred to as "glyceride mixture" below.

"Glyceride" within the meaning of the inventive process is further taken to mean derivatives derived from glycerol. In addition to the above described glycerides of fatty acids, these also include glycerophospholipids and glyceroglycolipids. Preference is given here to the glycerophospholipids such as lecithin (phosphatidylcholine), cardiolipin, phosphatidylglycerol, phosphatidylserine and alkylacylglycerophospholipids, such as plasmalogen. In particular, derivatives in which the fatty acid composition of the naturally-occurring non-conjugated or saturated glycerides has not substantially changed are included.

Preferred starting materials are particularly glycerides or mixtures of glycerides, in particular of mono-, di- or triglycerides, that are esterified with at least one, preferably two or three, polyunsaturated, in particular homoconjugated, fatty acids. Therefore, preference is given to synthetic or natural glycerides or glyceride mixtures which contain acyl radicals having from 1 to 22 carbons, preferably having 18 carbons. Particular preference is given to natural oils and fats which contain polyunsaturated homoconjugated acyl radicals having more than 16 carbons and less than 22 carbons, preferably from 18 to 20 carbons.

The term "oil" or "fat" is taken to mean a mixture of fatty acids that comprises unsaturated, non-conjugated, preferably homoconjugated, esterified fatty-acid(s), in particular linoleic acid. Preferably, the oil or fat has a high content of unsaturated, non-conjugated esterified fatty acid(s), in particular linoleic acid. Preferably, the content of unsaturated, non-conjugated esterified fatty acids is approximately 30%, more preference is given to a content of 50%, still more preference to a content of 60%, 70%, 80%, 90% or more. For determination, the fatty acid content can, for example, be determined by gas chromatography after converting the fatty acids into the methyl esters by transesterification. The oil or fat can comprise various other saturated or unsaturated fatty acids, for example calendic acid, palmitic acid, stearic acid, oleic acid etc. In particular, depending on the preparation method, the content of the various fatty acids in the oil or fat can vary. Each fatty acid profile is included by the inventive preparation, in particular fatty acid profiles which are produced in the production of oil from vegetable material. Preferably, the fatty acid esters are present as a glyceride, in particular as a triglyceride.

Preference is therefore given to an inventive process where the glyceride mixture can be of animal, microbial or vegetable origin, for example olive oil, canola oil, coconut oil, coconut fat, sesame seed oil, rice germ oil, bamboo oil, bamboo fat, sunflower seed oil, rapeseed oil, fish oil, tallow oil, soybean oil, palm oil, safflower oil, linseed oil, wheatgerm oil, peanut oil, cottonseed oil, corn oil, pig fat, beef fat, poultry fat, milk fat, tung oil or shea oil or a derivative or a mixture thereof. Particular preference is given in particular to oils and fats which have a high content of linoleic acid, for example sunflower seed oil, soybean oil, cottonseed oil, corn oil or wheatgerm oil, safflower oil, thistle oil, rapeseed oil and in particular oils or fats from modified plant cultivars, in particular what are termed high linoleic seeds, for example linola (from linseed oil). The modified plant cultivars can be bred or advantageously can also be produced by mutagenesis (for example GMO) (Angew. Chem. 2000, 112, 2292–2310).

The starting material for the inventive process can also be produced by conventional processes known to those skilled in the art, for example oil from plants. Oil can be produced by pressing, for example, seed having a high husk content, or husked seed. For pressing and production, in addition to vegetable seed, other plants parts, for example leaves, tubors, stems, blossoms, fruits etc. of suitable plants can also be used which have a high content of unsaturated fatty acids, preferably esterified in triglycerides. Whole plants can also be used. The pressed material can also be pressed repeatedly.

Other materials which are also suitable for producing oils and fats suitable for the inventive process are microorganisms, such as *Thraustochytrium* or *Schizochytrium* strains, algae such as *Phaeodactylum tricornutum* or *Crypthecodinium* species, ciliates, such as *Stylonychia* or *Colpidium*, fungi such as *Mortierella*, e.g. *Mortierella alpina*, *Entomorphthora* or *Mucor*. By means of strain selection, a number of mutant strains of the corresponding microorganisms have been developed that produce a series of desirable compounds, including PUFAs and which are also suitable for producing said fatty acids or oils. In particular microorganisms can be produced by suitable transformations, for example using nucleic acid molecules coding for desaturases or elongases.

Preferably, in the inventive process, linoleic ester is converted to conjugated linoleic ester (CLA).

Preference is therefore given to starting products which comprise linoleic esters, for example those which have a high content of linoleic acid-containing triglycerides. Particular preference is therefore given to processes in which natural oils and fats that have a high content of linoleic acid, as described above, are converted according to the invention, for example sunflower seed oil, soybean oil, safflower oil, linseed oil or derivatives of the same.

In an embodiment, in the inventive process, the catalysis is carried out using the compound I

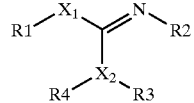

(I)

where independently of one another $X_1$ can be —NH— or —PH—, preferably —NH—, $X_2$ can be C, N or P, preferably N or P, most preferably N, and where R1 to R4 independently of one another can be:

H, branched or unbranched $C_1$- to $C_{20}$-alkyl, where from 0 to 3 carbons can be replaced by O, S, NZ and/or —$X_3$—(C=$X_4$)—, mono-, bi-, or tricyclic, aromatic, saturated or partially unsaturated $C_0$- to $C_6$-alkylcarbocycle or heterocycle having from 3 to 17 carbons, where from 0 to 3 heteroatoms can be selected from O, S, NZ and/or —$X_3$—(C=$X_4$)—;

and where each carbon of the alkyl chains or of the ring can bear up to three of the following substituents OZ, SZ, (C=O)—OZ, $NZZ_1$, $C_1$- to $C_6$-alkyl;

where $X_3$ can be a bond, O, S or NZ, and/or $X_4$ can be O, S or NZ; and where Z and/or $Z_1$ independently of one another can be H or $C_1$- to $C_6$-alkyl.

X1 and X2 can thus be part of a ring via R3 or R4, in particular R1 and R4, and R2 and R3, can be part of a ring. The rings can therefore bear heteroatoms or further double bonds. In particular, R1 and R4, and R2 and R3, can be cyclically linked via $(CH)_2n$, where n=2, 3, 4, 5.

It is known to those skilled in the art that the use of compound I where $X_1$ is —PH— is only possible under inert conditions that prevent oxidation of —PH—.

Compound I can also be polymer-bound, for example as Merrifield resins, for example heterogenized as Merrifield resins on various chloromethylated poly(styrene/divinylbenzene) resins, or heterogenized on polystyrene resin after introduction of a spacer in the form of an alkyl chain.

The catalyst can be present both as pure substance and immobilized, for example bound to a polymer (polymer-bound guanidine bases (J. Mol. Catal. A: Chemical 109 (1996) 37–44; Pure Appl. Chem., A29(3), 249–261 (1992)), polymer-bound aminoiminophosphorane bases (Chimia 39 (1985) No.9, 269–272) or incorporated into a support (cyclohexylguanidine in zeolite Y; THL, Vol. 38, No. 8, 1325–1328, 1997)).

Preferably, compound I has the following structure (Ia):

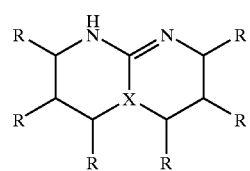

(Ia)

where X is C, N, or P, preferably N or P, most preferably N, and R is as defined above for R1 to R4.

Preference as catalyst is also given to compounds (II):

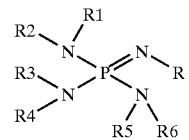

(II)

More preference is given to compounds (IIa):

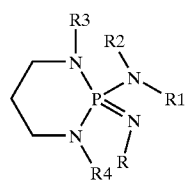

(IIa)

More preference is given to compound (IIb):

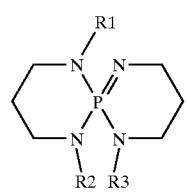

(IIb)

where in compounds (II) to (IIb), for R and R1 to R6, the same applies as above for R1 to R4.

In particular, R1 and R2, R3 and R4, and/or R5 and R6 can be cyclically linked.

Surprisingly, it was found in the inventive process that compound I or II, in particular imino bases or iminophosphazene bases, preferably aminoimino bases or aminoiminophosphazene bases, can catalyze the isomerization of non-conjugated polyunsaturated fatty acids in the glyceride without addition of protic solvents, for example alkyl alcohols. Particular preference is therefore given to carrying out the inventive process using guanidine bases, or the bases enumerated below, as catalyst.

Particular preference is given to 1,5,7-triazabicyclo[4.4.0]dec-5-ene (TBD) or analogous diaza bases, for example 1,2,3,4,4a,5,6,7-octahydro-1,8-naphthyridine [CAS 60832-40-8]. Most preference is given to TBD.

Particular preference is also given to the phosphazene base P4-T-BU [CAS 111324-04-0], phosphazene base P1-T-Oct No. [CAS 161118-69-0], phosphazene base P1-T-Bu-tris(tetramethylene) [CAS 161118-67-8], phosphazene base P2-T-Bu [CAS 111324-03-9], phosphazene base P4-T-Oct [CAS 153136–05–1], the salts 1,1,1,3,3,3-hexakis(dimethylamino)diphosphazenium fluoride [CAS 137334-

99-7], 1,1,1,3,3,3-hexakis(dimethylamino) diphosphazenium tetrafluoroborate [CAS 137334-98-6] or 2-tert-butylimino-2-diethylamino-1,3-dimethylperhydro-1,3,2-diazaphosphorine [CAS 98015-45-3].

The above salts (for example $BF_3^-$, or $F^-$ salt) or other salts of said compounds are also claimed.

Preferred solvents for carrying out the inventive process are nonprotic, for example ethyl esters, hexane, heptane, DMSO, DMF, MTBE, or THF. However, those skilled in the art, on the basis of the disclosure of the present invention, can find by simple test series other solvents which can also advantageously be used in the inventive process. The inventive process, however, can also be carried out with the addition of protic solvents, for example alkyl alcohols.

Conjugated fatty acids and their esters are preferably used in drugs or foodstuffs for humans and animals and in cosmetics. Therefore, it is advantageous to carry out the inventive process using solvents which are nontoxic, or are of as low toxicity as possible, so that it is not necessary to separate off the solvent after carrying out the process, or slight traces are not hazardous for the desired use.

Depending on use, a different solvent can be advantageous. For example protic solvents, for example methanol, ethanol etc., can also be used, for example for conjugating esters of unsaturated homoconjugated fatty acids. It can be advantageous to use a solvent which can be readily separated off from the fatty acids, glycerides, oils or fats, for example can be extracted by shaking in water or which is low-boiling, for example MTBE.

Advantageously, the inventive process can be carried out without solvent. The reaction temperature of the process must then be adapted so that the melting point of the catalyst used is exceeded. It can be advantageous to carry out the process at low temperatures and to dissolve the catalyst in a suitable solvent for this. However, from economic aspects, it can also be advantageous not to use solvent.

Advantageously, the inventive process is carried out at temperatures below 180° C. High temperatures in the isomerization lead to lower yields, for example owing to derivatizations or destruction of the fatty acids. The temperature of the inventive process can be chosen differently, depending on solvent, catalyst, pressure and starting material.

The temperature and reaction time depend, for example, on the strength of the base used. Thus TBD is a strong guanidine base, but the reaction temperature, owing to the high melting point, must be chosen to be above 130° C. if no solvent is used. Preferably the temperature in the case of, for example, guanidine bases such as TBD without solvent, is above the melting point but below 200° C., for example from 120° C. to 180° C., more preferably from 120° C. to 160° C., still more preferably from 130° C. to 140° C. The reaction times should be chosen accordingly. If a solvent is used the reaction temperature and reaction time can be adapted. Via simple series of experiments those skilled in the art can establish the yield and the amount of by-products, in particular of unwanted isomers, and harmonize the experimental conditions accordingly. The same applies to employing other catalysts used according to the invention. Thus the phosphazene bases, depending on conditions, react at as low as 0° C., but, from energetic aspects, higher temperatures are preferred, for example room temperature. Those skilled in the art could accordingly exchange the base selected, change the temperature or adapt the reaction time, if too many by-products occur. It is thought that the amount of by-products, in particular the trans/transfatty acids, is caused by a frequent change between deprotonation and protonation. The examples show how those skilled in the art can derive suitable experimental conditions from the combination and variation of various parameters.

Furthermore, the inventive process can be carried out continuously or batchwise.

The inventive process can be carried out not only batchwise, but also continuously. For the continuous procedure, a tubular reactor, for example, can be used, in which the catalyst capable of isomerization is present. The catalyst can be present not only as pure substance, but also immobilized, for example bound to a polymer (polymer-bound guanidine bases (J. Mol. Catal. A: Chemical 109 (1996) 37–44; Pure Appl. Chem., A29(3), 249–261 (1992); polymer-bound aminoiminophosphorane bases (Chimia 39 (1985) No. 9, 269–272) or incorporated into a support (cyclohexylguanidine in zeolite Y; THL, Vol. 38, No. 8, 1325–1328, 1997)). Continuous reaction of vegetable oils with polymer-bound guanidine bases is described in BR 8202429.

In addition, a process is included according to the invention in which the catalyst is separated off in a further step.

In order that the product of the inventive process can be used as a food additive for humans and animals, it can be expedient to separate off the solvents and catalysts used.

The solvent can be separated off by distillation or removal by aqueous extraction. The same applies to the catalysts.

In one step, in the inventive process, the fatty acid can be cleaved off. Also, in one step of the process, the fatty acid can be transesterified. Corresponding processes are known to those skilled in the art and are described above. These steps can be carried out subsequently or simultaneously with the described process steps.

In a further embodiment, the present invention relates to the product of the inventive process, in particular to a conjugated alkene, for example in particular in the form of a glyceride, but also in other forms, as are included under the above description for "alkenes", for example as fatty acids, esterified fatty acids, for example glycerides, also mixtures of different alkenes which are used as starting material, or a glyceride mixture obtainable by the inventive process, the product still being able to contain e.g. the catalyst, preferably in nontoxic amounts.

The inventive product comprises the abovementioned catalyst, for example even only in traces, or has been prepared from a natural glyceride mixture, for example one of the abovementioned oils or fats, or a mixture or a derivative thereof, or from a complex synthetic oil or fat.

"Complex synthetic oil or fat" is taken to mean those oils or fats which consist of more than one glyceride or of one or more mono- or diglycerides, for example of glycerides that have at least one identical or different fatty acids bound in one or different esters of the glyceride, or that have at least two different fatty acids, or the fatty acids of which are bound to different carbons of the glyceride (for example 1,2 and 1,3 glycerides), or triglycerides of at least two different fatty acids.

Complex synthetic oils or fats are, in particular, those oils and fats that have glycerides or mixtures of glycerides which, after cleavage of the fatty acids, can no longer be prepared in the same structure and in the same composition. The processes described in the prior art make possible the synthesis (isomerization) of polyunsaturated fatty acids that are esterified with a glyceride only after cleavage or transesterification, conjugation and reesterification with glycerides or glycerol. As a result the structure of the glycerides in the prepared mixtures, oils or fats and their composition change. Glyceride mixtures which are obtainable by the inventive process, however, have essentially the same composition as the starting mixture, but the polyunsaturated fatty acids (for example linoleic acid), owing to the inventive process, are conjugated to an increased extent (for example to form CLA). Advantageously, in particular, the CLA content in the product is increased. The composition of the residual fatty acids and, in particular, of the non-conjugated fatty acids esterified with glycerides, is essentially unchanged in the product.

Therefore, the present invention relates to a glyceride mixture in which the content of conjugated fatty acids is higher than the content of conjugated fatty acids of the starting glyceride mixture, and the further composition, for example of the glycerides, saturated fatty acids and/or esters of fatty acids, essentially corresponds to the composition of the starting glyceride mixture.

The term "essentially correspond to the composition of the starting glyceride" also includes changes as occur when the inventive process is carried out, for example on account of the increased pressure, the reaction with a solvent or the high temperature, without addition of catalyst. The term "starting glyceride mixture" is also taken to mean, in particular, natural and complex synthetic oils and fats, preferably rich in glycerides, in particular in triglycerides. However, the mixtures can also have a content of free fatty acids and other additives, as are listed above, for example. To prepare CLA, the "starting glycerides" are rich in linoleic acid. Examples of preferred natural oils are enumerated above. The term "starting glyceride mixture" also includes mixtures of different oils and fats.

Of economic advantage for the isolation of CLA is a glyceride mixture as product in which the content of conjugated linoleic acid is at least 30%, preferably 50%, more preferably 60%, 70% or 80%, most preferably more than 90%, of the content of linoleic acid of the starting glyceride mixture. However, small amounts of CLA in the oils or fats can also be advantageous, for example in food additives.

Preferably, the inventive glyceride mixture has contents of 11,13-octadecadienoic acid isomers, 8,10-octadecadienoic acid isomers, cis,cis-octadecadienoic acid isomers and/or trans/trans-octadecadienoic acid isomers in each case less than 5%, more preferably less than 3%, most preferably 1% or less, of the fatty acid content.

Particular preference is given to glyceride mixtures in which the CLA content in the triglyceride is greater than 30%, more preferably greater than 50%, 60% or 70%, most preferably greater than 80% or 90%, and which have a content of less than 5%, more preferably less than 3%, most preferably 1% or less, of 11,13-octadecadienoic ester isomers, 8,10-octadecadienoic ester isomers, cis,cis-octadecadienoic ester isomers and/or trans/trans-octadecadienoic ester isomers. The CLA content in the triglyceride of greater than 50% consists here principally of C18:2 cis-9, trans-11 and C18:2 trans-10, cis-11 CLA in a ratio of 1:1.

Further preference is given to a glyceride mixture in which the CLA content in the triglyceride essentially consists of cis-9, trans-11 and trans-10, cis-12 CLA.

The isoforms cis-9, trans-11 and trans-10, cis-12 CLA appear to be the biologically active isoforms of CLA, therefore mixtures which have a high content of these two isoforms and a lower content of those isoforms which have been enumerated above are particularly advantageous. The inventive mixtures are particularly suitable for those applications in which high contents of CLA are advantageous, for example to produce cosmetics, drug, food or animal feed preparations or a remedy.

In a further embodiment the present invention relates to a cosmetics, food, food supplement, animal feed or drug preparation which comprises an inventive product, in particular the inventive alkene, for example as glyceride or glyceride mixture. Inventive alkenes, for example glycerides, can only be added such that the content of catalyst is harmless for the intended usage.

Said preparation can therefore contain additives.

The term "additives" is taken to mean further additives which are advantageous for nutrition or health, for example "nutrients" or "active compounds". The preparation can comprise one or more additives for animal or human nutrition or treatment and can be diluted or mixed therewith. Additives can be administered together with, or separately from, the feed, food, food supplement or drug. A food, food supplement, animal feed or drug preparation contains no additives, or no quantities of additives, which may be considered harmful for animal or human nutrition.

"Nutrients" are those additives which are advantageous for the nutrition of humans or animals. Preferably, the inventive preparation therefore also comprises vitamins, for example vitamins A, $B_1$, $B_2$, $B_6$, $B_{12}$, C, $D_3$, K and/or E, pantothenic acid, biotin, choline, folic acid, nicotinic acid, taurine, carboxylic acids, for example tricarboxylic acids, citrate, isocitrate, trans/cis aconitate, and/or homocitrate, enzymes, for example phytases, carotenoids, minerals, for example P, Ca, Mg and/or Na, proteins, carbohydrates, fats, amino acids and/or trace elements Mn, Zn, Cu, Co, Se, Fe and/or Cr. The preparation can also comprise pyruvic acid, L-carnitine, carbohydrases, lipoic acid, coenzymes Q10, aminocarboxylic acids, for example creatine.

"Active compounds" are substances which support the use of the inventive preparation as drug or serve for their action in the treatment of disorders, in particular in the treatment of cancer, diabetes, overweight, AIDS, allergies and cardiovascular disorders (see also below).

Therefore the inventive preparation can also include preservatives, antibiotics, antimicrobial additives, antioxidants, chelating agents, inert gases, physiologically harmless salts etc. Those skilled in the art know the additives suitable to add to the preparation for the respective use as drug, animal feed, food supplement or food additive, or can determine them by simple tests known in the prior art.

"Additives" are also antioxidants. Antioxidants are advantageous, for example, to protect the double bonds of the fatty acids from oxidation. However, the general health-promoting action of antioxidants is also known. Thus, in animal nutrition, ethoxyquin, BHT and/or BHA are used as antioxidants, otherwise, gamma- and alpha-tocopherols, tocotrienol, rosemary extract, naturally occurring polyphenols, for example flavonoids, isoflavones and carotenoids, are also used.

In a further embodiment, said preparation comprises further polyunsaturated fatty acids (PUFAs). Preferably, the preparation comprises omega-3-fatty acids, for example alpha-linolenic acid, docosahexaenoic acid, docosapentaenoic acid, and/or eicosapentaenoic acid, dimorphecolic acid, parinaric acid, and/or calendic acid, and/or omega-6-fatty acids, for example linoleic acid, gamma-linolenic acid, and/or dihomo-gamma-linolenic acid.

The inventive preparation can be solid, for example readily soluble in water or oils, or liquid. The preparation, depending on use, has the appropriate dosage form, for example for animal nutrition, as food additive or as drug. Such dosage forms are, for example, tablets, capsules, powders, granules, sugar-coated tablets, solutions, nutrient-defined/balanced diets, such as enteral formula, and preparations for infant nutrition, fat emulsions for parenteral nutrition, etc. Advantageous dosage forms of the preparations for the respective application are known to those skilled in the art. The fatty acids can be in free form, present as ethyl or methyl esters or preferably, however, as triglyceride.

Flavorings can also be added to said preparations.

In foods, the preparation can be combined with customary food components. These include vegetable and animal products, in particular sugars, if appropriate in the form of syrups, fruit preparations, such as fruit juices, nectar, fruit pulps, purees or dried fruits; cereal products and starches of said cereals; milk products, such as milk protein, whey, yoghurt, lecithin and lactose.

The inventive preparation is also suitable for use in animal nutrition and can comprise, for example, additives.

"Additives" are taken to mean substances which serve for improving product properties, such as dust behavior, flow properties, water absorption capacity and storage stability. Examples of such additives and/or mixtures thereof can be those based on sugars, for example lactose or maltodextrin, based on cereal products or legume products, for example corncob grit, wheat bran and soybean meal, based on mineral salts, inter alia calcium salts, magnesium salts, sodium salts, potassium salts, and also D-pantothenic acid or its salts themselves (salt of D-pantothenic acid prepared chemically or by fermentation).

The present invention further relates to preparations which comprise inactive, viable and/or growing contents of organisms producing triglycerides or other additives. Preferably, these are microorganisms, preferably fungi, yeasts and/or bacteria. Particularly preferably, the inventive-animal-feed comprises inactive, viable and/or growing contents of fungi of the genus Mucor, yeasts of the genus Saccharomyces and/or bacteria of the Enterobacteriaceae, such as *E. coli, Proteus vulgaris, Pseudomonads*, such as *Pseudomonas matophila, Bacillaceae*, such as *Bacillus subtilis* or *Bacillus cereus, Coryneform bacteria*, such as *Corynebacterium glutamicum* or *Brevibacterium breve* and/or *Actinum mycetalis* and/or mixtures thereof. Very particular preference is given to bacteria of the genus *Bacillus* and, in this case, the species *Bacillus subtilis*. Also, genetically modified and/or transgenic organisms and/or production strains suitable for producing the polyunsaturated fatty acids are included in the invention. The enumeration above is not limiting here for the present invention.

If the inventive products, in particular the inventive alkene or glyceride mixtures are administered individually or in combination in feeds, the active compounds are administered as pure substance or as mixtures of substances or liquid or solid extracts together with customary feed constituents. Examples of customary feed constituents are: corn, barley, wheat, oats, rye, triticale, sorghum, rice and brans, semolina brans and flours of these cereals, soybeans, soybean products such as soybean extraction meal, rapeseed, rapeseed extraction meal, cottonseed and extraction meal, sunflower seed, sunflower seed extraction meal, linseed, linseed extraction meal, expeller meals of oil seeds, field beans, peas, gluten, gelatin, tapioca, yeasts, single cell protein, fish meal, salts, minerals, trace elements, vitamins, amino acids, oils/fats and the like. Advantageous compositions are described, for example, in Jeroch, H. et al. Ernährung landwirtschaftlicher Nutztiere [Farm animal nutrition], Ulmer, UTB.

The inventive preparation can be powder, granules, pellet, coated extrudate and/or as a combination thereof. The preparation of the inventive animal feed, for example by means of coating compounds, serves, for example, for improving product properties, such as dust behavior, flow properties, water absorption capacity and storage stability. Such preparations are extensively known in the prior art. Thus, in animal nutrition, for example, blocks of a solid, cohesive shape-retaining mix of several kilos are used.

Animal nutrition preparations are composed in such a manner as to cover optimally the appropriate nutrient requirement for the respective animal species. Generally, plant feed components such as cornmeal, wheat meal or barley meal, soybean whole meal, soybean extraction meal, linseed extraction meal, rapeseed extraction meal, green flour or ground peas, are chosen as sources of crude protein. In order to ensure an appropriate energy content of the feed, soybean oil or other animal or vegetable fats are added. Since the plant protein sources contain some essential amino acids only in an inadequate amount, feeds are frequently enriched with amino acids. This is primarily with lysine and methionine. In order to ensure the mineral and vitamin supply of the farm animals, in addition, minerals and vitamins are added. The type and amount of added minerals and vitamins depends on the animal species and is known to those skilled in the art (see, for example, Jeroch et al., Ernährung landwirtschaftlicher Nutztiere, Ulmer, UTB). To cover the nutrient and energy requirements, complete feeds can be used which comprise all nutrients in a ratio to one another covering requirements. It can form the sole feed of the animals. Alternatively, a supplementary feed can be added to a cereal grain feed. This relates to protein-, mineral- and vitamin-rich feed mixtures that usefully supplement the grain feed.

In addition, the invention relates to an inventive preparation that is a drug. The combinations mentioned herein can advantageously be used in the manufacture of drugs for treating cancer, allergies, diabetes and/or cardiovascular disorders, for example arteriosclerosis. A process for producing cosmetics, drugs or remedies can comprise one of the steps of the inventive process and formulation of the process product into a pharmacologically or dermatologically compatible form. Also, an inventive alkene, glyceride or glyceride mixture can be formulated into a pharmacologically or dermatologically compatible form.

Improved food conversion, as has been observed for CLA, can lead to more rapid convalescence, for example, in the case of persons or animals weakened by illness. The drugs prepared using the inventive preparation can therefore also be used for the treatment of cancer, cardiovascular disorders, for example arteriosclerosis (MacDonald, J. J. American College of Nutrition, (2000) 19, 111S–118S), diabetes (WO99/29317), allergies, overweight and for disorders accompanying diets.

Thus, for example, the use of said preparation to accelerate build-up of the body, for example after a relatively long illness, which is accompanied by loss of weight, for example chemotherapy, and to support or accelerate the convalescence process is advantageous.

The drug can, in addition, comprise other active compounds, for example the abovementioned or other active compounds. The active compounds can be used to treat cancer, cardiovascular disorders, for example arteriosclerosis, diabetes, allergies, and to support diets or improve the action of the inventive preparation. A drug for treating diabetes can comprise, for example, insulin, sulfonylureas, sulfonamides, lipoic acid, gamma-glucosidase inhibitors, thiazolidinediones, metformin and/or acetylsalicylic acid. Cancers are treated, for example, by adding cytostatics, such as vinca alkaloids, alkylating agents, for example chlorambucil, melphalan, thio-TEPA, cyclophosphamide, etc., by folic acid analogs, such as aminopterin or methotrexate, or by the addition of immunosuppressives, for example cyclophophosphamide and azathioprine, glucocorticoids, such as prednisolone, or cyclosporin. HIV infections or AIDS can be treated, for example, by administering reverse transcriptase inhibitors and/or protease inhibitors. Allergies are treated, for example, by stabilizing the mast cells, for example using chromoglyxate, by blockading the histamine receptors, for example by H1-antihistamines, or by functional antagonists of the allergy mediators, for example by alpha-sympathomimetics, adrenalin, beta2-sympathomimetics, theophylline, ipratropium or glucocorticoids. Cardiovascular disorders are treated using coagulation inhibitors, ACE inhibitors, cholesterol-lowering agents, such as statins and fibrates, niacin, cholestyramine.

The drug can comprise a pharmaceutically compatible carrier. Examples of suitable pharmaceutically compatible carriers are known in the prior art and include physiologically harmless salts, for example phosphate-buffered salines, water, emulsions, for example oil/water emulsions, sterile solutions, etc. Sterile solutions can be, for example, aqueous or non-aqueous solutions. Aqueous solutions are, for example, water, alcohol/water solutions, emulsions or suspensions, and include sodium chloride solutions, Ringers dextrose, dextrose and sodium chloride etc. Examples of non-aqueous solutions are propylenes, glycol, polyethylene glycol, vegetable oils, organic esters, for example ethyl oleate. In addition, the drug can comprise one of the above-mentioned suitable additives.

Drugs can be administered in a conventional manner orally or parenterally (subcutaneously, intravenously, intramuscularly, intraperitoneally). They can also be administered via the nasal/throat cavity via vapors or sprays.

The dosage depends on age, condition and weight of the patient, and also on the type of administration. Generally, the daily active compound dosage is from about 0.05 to 100 mg/kg of body weight for oral administration and from about 0.01 to 20 mg/kg of body weight for parenteral administration. Particular preference is given to from 0.5 to 50 mg/kg.

The novel compounds can be used in the solid or liquid state in the conventional pharmaceutical dosage forms, for example as tablets, film tablets, capsules, powder, granules, sugar-coated tablets, suppositories, solutions, lotions, creams or sprays. These are manufactured in a conventional manner. The active compounds in this case can be processed together with the customary pharmaceutical aids, such as tablet binders, fillers, preservatives, tablet disintegrators, viscosity controlling agents, emollients, wetting agents, dispersants, emulsifiers, solvents, retarding agents, antioxidants and/or propellant gases (see H. Sucker et al.: Pharmazeutische Technologie [Pharmaceutical technology], Thieme-Verlag, Stuttgart, 1991). The resultant dosage forms comprise active compounds usually in an amount from 0.1 to 90% by weight.

An inventive drug can be manufactured, for example, by producing crude extracts from plants that comprise unsaturated esterified fatty acids, in particular triglycerides, for example in the form of the abovementioned oils and fats, reacting them and formulating them. Standard manufacturing processes for drugs are sufficiently known to those skilled in the art.

Depending on purpose, the amount of glyceride used, for example the CLA used, must be adapted. The amount of glyceride used can be, for example, 0.01 or 0.1% of the amount of fat added during feeding. Preference is also given to 0.5%, 1%, 2% or 3%, 5% or 10% glyceride, in particular CLA.

In the case of animal nutrition preparations, the proportion of the oils/fats added to the amount of fat during feeding can be up to 100%. If the amount of fat added is based on the fat content analyzed in the feed (total fat), the proportion of CLA can be 75% or less.

In a further embodiment the present invention also relates to a kit which comprises the inventive preparation. The preparation can be packed in one or more containers. The constituents of the inventive preparation, for example the alkene, glyceride or glyceride mixture, but also the abovementioned additives, can be packed separately or together in one container of the kit. The kit can be used for carrying out the inventive process and contain instructions for carrying it out.

Various documents are cited in the present text of this description. Each of the documents (including instructions and descriptions of manufacturers) is hereby incorporated in the description by reference. This does not mean, however, that each of said documents is actually prior art for the present invention.

The present invention is explained by the following examples and drawings, without these restricting this present invention in any manner.

EXAMPLES 1. 100 g of thistle oil (Cereol, contains 72% of linoleic acid) are heated with 10 g of 1,5,7-triazabicyclo[4.4.0]dec-5-ene (TBD) under argon for 6 hours at 135° C. The mixture is allowed to come to room temperature and the solution is made acid using 1N HCl. The reaction solution is washed twice with 350 ml of water. The remaining organic phase is taken up in dichloromethane and concentrated at 50° C. and 7 mbar on a rotary evaporator. Since the resultant oil, in the form of the triglyceride, cannot be analyzed by GC, it is reacted with potassium ethoxide in ethanol to give the ethyl esters of the fatty acids.

GC result (fatty acids as ethyl esters): palmitic acid 6.8%; stearic acid 3.1%, oleic acid 14.5%, 9-cis,11-trans conjugated linoleic acid 35.4%, 10-trans,12-cis conjugated linoleic acid 35.8%.

2. In a reaction block, in each case 10 g of the ethyl ester of a fatty acid, produced by transesterification of sunflower seed oil, having a content of 9cis,12cis-linoleic acid ethyl ester of 66% were heated with 1 g of the respective base at 130° C. The product was analyzed by GC. The percentage peak areas are shown.

| Catalyst | LA EE [area %] | CLA EE [area %] |
|---|---|---|
| 2-tert-Butyl-1,1,3,3-tetramethylguanidine (Barton base) | 65.7 | 0.0 |
| 1,5,7-Triazabicyclo(4.4.0)dec-5-ene | 0.0 | 63.5 |
| 1,3,4,6,7,8-Hexahydro-1-methyl-2H-pyrimidino-(1,2A)-pyrimidine | 65.9 | 0.0 |
| 2-tert-Butyl-2-diethylamino-1,3-dimethylperhydro-1,3,2-diazaphosphorine | 65.9 | 0.0 |

3. 9cis,12cis-Linoleic acid ethyl ester (Aldrich, 98%), and trilinolein (Aldrich) were reacted with various bases: analysis was performed by GC. The peak areas are shown.

| No. | Starting material | Base | Proportion of base to fatty acid residue | Solvent | Reaction time/temp. | Analysis as | Starting material | Linoleic acid | CLA 9c11t | CLA 10t12c | CLA cis/cis | CLA trans/trans |
|---|---|---|---|---|---|---|---|---|---|---|---|---|
| 1 | LA-EE | Phosphazene base P4-t-Bu solution (1M in hexane) | 120 mol % | THF | 30 min at 30° C. | Ethyl ester | 28.1 | — | 32.7 | 36.1 | 0.6 | 0.6 |
| | | | | | 60 min at 30° C. | Ethyl ester | 11.1 | — | 40.3 | 44.9 | 0.7 | 0.8 |
| | | | | | 30 min at 0° C. | Ethyl ester | — | — | 45.1 | 51.5 | 0.8 | 1.5 |
| | | | | | 60 min at 0° C. | Ethyl ester | — | — | 45 | 51 | 0.8 | 2.1 |
| | | | | | 30 min at 20° C. | Ethyl ester | — | — | 43.7 | 49.4 | 0.8 | 5.1 |
| | | | | | 120 min at 20° C. | Ethyl ester | — | — | 37.9 | 43.9 | 1 | 16 |
| 2 | LA-EE | Phosphazene base P4-Bu solution (1M in hexane) | 10 mol % | without solvent | 1 h at 0° C. | Ethyl ester | — | — | 46 | 48.8 | 0.9 | 1.4 |
| | | | | | 2 h at 0° C. | Ethyl ester | — | — | 46.4 | 49.8 | 1 | 2 |
| | | | | | 1 h at 20° C. | Ethyl ester | — | — | 42.3 | 45.9 | 1 | 3.6 |
| | | | | | 2 h at 20° C. | Ethyl ester | — | — | 45.2 | 48.8 | 1 | 4.1 |
| | | | | | 1 h at 80° C. | Ethyl ester | — | — | 44.9 | 48.5 | 1 | 4.9 |
| | | | | | 1 h at 120° C. | Ethyl ester | — | — | 44.8 | 48.4 | 1 | 4.9 |
| 3 | LA-EE | 1,8-Diazabicyclo[5.4.0]-undec-7-ene | 10 mol % | without solvent | 1 h at 120° C. | Ethyl ester | 98.6 | — | — | — | — | — |
| 4 | Trilinolein | Phosphazene base P4-Bu solution (1M in hexane) | 10 mol % | without solvent | 1 h at 0° C. | Ethyl ester | 73.5 | — | 11.4 | 13.7 | — | — |
| 5 | LA-EE | 1,8-Bis(dimethyl-amino)naphthalene | 10 mol % | without solvent | 1 h at 0° C. | Ethyl ester | 99.4 | — | — | — | — | — |
| | | | | | 1 h at 20° C. | Ethyl ester | 99.2 | — | — | — | — | — |
| | | | | | 2 h at 20° C. | Ethyl ester | 99.3 | — | — | — | — | — |
| | | | | | 1 h at 80° C. | Ethyl ester | 99.5 | — | — | — | — | — |
| | | | | | 1 h at 120° C. | Ethyl ester | 99 | — | — | — | — | — |
| 6 | LA-EE | 1,3,4,6,7,8-Hexahydro-1-methyl-2H-pyrimido-[1,2-a]pyrimidine | 10 mol % | without solvent | 1 h at 0° C. | Ethyl ester | 99.3 | — | — | — | — | — |
| | | | | | 1 h at 20° C. | Ethyl ester | 99.2 | — | — | — | — | — |
| | | | | | 2 h at 20° C. | Ethyl ester | 99.3 | — | — | — | — | — |
| | | | | | 1 h at 80° C. | Ethyl ester | 99.6 | — | — | — | — | — |
| | | | | | 1 h at 120° C. | Ethyl ester | 99 | — | — | — | — | — |
| 7 | LA-EE | 1,5,7-Triazabicyclo-[4.4.0]dec-5-ene | 10 mol % | without solvent | 1 h at 0° C. | Ethyl ester | 99.5 | — | — | — | — | — |
| 8 | Trilinolein | Phosphazene base P4-Bu solution (1M in hexane) | 10 mol % | without solvent | 1 h at 20° C. | Ethyl ester | 39.7 | — | 19.8 | 24 | — | — |
| 9 | Trilinolein | 1,5,7-Triazabicyclo-[4.4.0]dec-5-ene | 10 mol % | toluene | 4 h at 110° C. | Ethyl ester | 71.6 | — | 10.4 | 12.5 | — | — |
| 10 | Trilinolein | 1,5,7-Triazabicyclo-[4.4.0]dec-5-ene bound to polystyrene | 10 mol % | toluene | 4 h at 110° C. | Ethyl ester | 96.2 | — | — | — | — | — |
| 11 | LA-EE | 1,8-Diazabicyclo-[5.4.0]undec-7-ene | 10 mol % | toluene | 2 h at 110° C. | Ethyl ester | 99.2 | — | — | — | — | — |
| | | | | | 4 h at 110° C. | Ethyl ester | 99.5 | — | — | — | — | — |
| | | | | | 6 h at 110° C. | Ethyl ester | 99.4 | — | — | — | — | — |
| 12 | LA-EE | 1,5,7-Triazabicyclo-[4.4.0]dec-5-ene | 10 mol % | toluene | 2 h at reflux | Ethyl ester | 76.4 | — | 10.7 | 12 | — | — |
| | | | | | 4 h at reflux | Ethyl ester | 60 | — | 18.4 | 20.1 | — | — |
| | | | | | 6 h at reflux | Ethyl ester | 47.6 | — | 24.3 | 26.1 | — | — |
| 13 | LA-EE | 1,3,4,6,7,8-Hexahydro-1-methyl-2H-pyrimido-[1,2-a]pyrimidine | 10 mol % | toluene | 2 h at reflux | Ethyl ester | 99.4 | — | — | — | — | — |
| | | | | | 4 h at reflux | Ethyl ester | 97.8 | — | — | — | — | — |
| | | | | | 6 h at reflux | Ethyl ester | 98.9 | — | — | — | — | — |

4. Linoleic acid methyl ester (66%) is continuously reacted with 1,5,7-triazabicyclo[4.4.0]dec-5-ene (TBD) in a tube at 150° C. to give conjugated linoleic acid methyl ester:

440.7 g of linoleic acid methyl ester (65.8%) and 49.9 g of TBD (Fluka, 98%) are charged into a flask under argon at room temperature and pumped through a steel coil (internal diameter 8 mm) heated to 150° C. The dead volume in the steel coil is 90 g.

| No. | Linoleic acid ethyl ester | CLA-M E 9c11t [area %] | CLA-M E 10t12c [area %] | Cis, cis-CLA isomers [area %] | Trans, trans-CLA isomers [area %] | Reaction time in the steel coil |
|---|---|---|---|---|---|---|
| 1 | 31.5 | 16.9 | 16.9 | 0.7 | 0.3 | approximately 26 min. |
| 2 | 17.8 | 23.7 | 23.6 | 1.0 | 0.4 | approximately 68 min. |

5. Repetition of the transesterification of vegetable oil with 1,5,7-triazabicyclo[4.4.0]dec-5-ene (TBD) according to the instructions of Schuchardt et al., *J. Braz. Chem. Soc.*, Vol. 9, No. 3, 199–210, 1998:

80.1 g (0.091 mol, equivalent to 0.27 mol of fatty acids) of sunflower seed oil (Bonita) are heated at 70° C. for 2 hours with 20 g (0.62 mol) of methanol and 0.31 g (0.002 mol, equivalent to 1 mol %) of 1,5,7-triazabicyclo[4.4.0]dec-5-ene (Fluka). The transesterification was followed using GC. No conjugated linoleic acid (CLA) was formed.

Analysis:

| Reaction time (min) | Palmitic acid C16:0 | Stearic acid C18:0 | Oleic acid C18:1 | Linoleic acid C18:2 | CLA |
|---|---|---|---|---|---|
| 20 | 6.1 | 4.6 | 23.0 | 63.8 | n.d. |
| 60 | 6.1 | 5.1 | 22.8 | 63.9 | n.d. |
| 90 | 6.1 | 4.4 | 23.5 | 64.0 | n.d. |
| 120 | 6.1 | 4.8 | 23.1 | 64.0 | n.d. | n.d. not detectable

6. Linoleic acid methyl ester (64.4%) is continuously reacted with 1,5,7-triazabicyclo[4.4.0.]-dec-5-ene (TBD) in a tube at 150° C. to give conjugated linoleic acid methyl ester:

223.8 g of linoleic acid methyl ester (64.4%) and 25.3 g of TBD (Fluka, 98%) are charged into a flask under argon at room temperature and pumped through a steel coil (internal diameter 2 mm) heated to 150° C. The dead volume in the steel coil is 11.7 mL. This corresponds to approximately 9.4 g. The pumping rate was set at 3 g/h.

| No. | Time from | Time to | Linoleic acid methyl ester | CLA-ME 9c11t [Area %] | CLA-ME 10t12c [Area %] | Cis, cis-CLA isomers [Area %] | cis, cis-CLA isomers [Area %] | Product weight [g] | Reaction time in the steel coil [h] |
|---|---|---|---|---|---|---|---|---|---|
| 1 | 7:40 | 8:30 |  | 20.8 | 20.7 | 0.9 | 0.3 | — | — |
| 2 | 8:30 | 9.30 |  | 26.4 | 26.3 | 1.0 | 0.3 | 6.5 | — |
| 3 | 9:30 | 10:30 |  | 29.0 | 28.9 | 1.2 | 0.4 | 3.3 | 3 |
| 4 | 10:30 | 11:30 |  | 30.1 | 30.0 | 1.3 | 0.0 | 2.1 | 4 |
| 5 | 11:30 | 12:30 |  | 29.9 | 29.8 | 1.2 | 0.4 | 3.0 | 3 |

7. Linoleic acid methyl ester (64.4%) is heated with 1,5,7-triazabicyclo[4.4.0.]-dec-5-ene (TBD) and toluene under reflux (115° C.).

11.2 g of linoleic acid methyl ester (64.4%; 0.025 mol), 1.05 g of TBD (Fluka, 98%; 0008 mol) and 11.2 g of toluene (0.12 mol) are charged into a flask under argon at room temperature and then heated under reflux (115° C.).

| Reaction time [h] | Linoleic acid methyl ester | CLA-ME 9c11t [Area %] | CLA-ME 10t12c [Area %] | Cis, cis-CLA isomers [Area %] | Trans, trans-CLA isomers [Area %] |
|---|---|---|---|---|---|
| 1 | 60.8 | 2.7 | 2.6 | — | — |
| 2 | 56.3 | 4.4 | 4.4 | — | — |
| 3 | 49.1 | 8.5 | 8.4 | — | — |
| 4 | 43.3 | 12.0 | 11.8 | — | — |
| 5 | 36.9 | 14.9 | 14.8 | — | — |
| 6 | 31.5 | 17.5 | 17.4 | — | — |

8. Linoleic acid methyl ester (64.4%) is heated with 1,5,7-triazabicyclo[4.4.0.]-dec-5-ene (TBD) and xylene (mixture of o, m and p-xylene) under reflux (145° C.).

11.5 g of linoleic acid methyl ester (64.4%; 0.026 mol), 1.04 g of TBD (Fluka, 98%; 0.008 mol) and 11.3 g of xylene (0.11 mol) are charged into a flask under argon at room temperature and then heated under reflux (145° C.).

| Reaction time [h] | Linoleic acid methyl ester | CLA-ME 9c11t [Area %] | CLA-ME 10t12c [Area %] | Cis, cis-CLA isomers [Area %] | Trans, trans-CLA isomers [Area %] |
|---|---|---|---|---|---|
| 1 | 34.9 | 16.0 | 15.9 | — | — |
| 2 | 16.3 | 24.7 | 24.6 | — | — |
| 3 | 9.4 | 28.1 | 28.0 | — | — |
| 4 | 5.0 | 30.4 | 30.2 | — | — |
| 5 | 2.6 | 31.5 | 31.3 | — | — |
| 6 | 1.5 | 32.0 | 31.8 | — | — |

9. Linoleic acid methyl ester (64.4%) is heated to 140° C. with 1,5,7-triazabicyclo[4.4.0.]-dec-5-ene (TBD) and diethylene glycol dimethyl ether.

11.6 g of linoleic acid methyl ester (64.4%; 0.026 mol), 1.05 g of TBD (Fluka, 98%; 0.008 mol) and 11.5 g of DEGDM (0.09 Mol) are charged into a flask under argon at room temperature and then heated to 140° C.

| Reaction time [h] | Linoleic acid methyl ester | CLA-ME 9c11t [Area %] | CLA-ME 10t12c [Area %] | Cis, cis-CLA isomers [Area %] | Trans, trans-CLA isomers [Area %] |
|---|---|---|---|---|---|
| 1 | 40.9 | 9.7 | 9.6 | — | — |
| 2 | 19.5 | 21.1 | 21.0 | — | — |
| 3 | 10.9 | 25.4 | 25.3 | — | — |
| 4 | 6.8 | 26.0 | 25.9 | — | — |
| 5 | 5.6 | 28.6 | 28.5 | — | — |
| 6 | 4.2 | 28.8 | 28.7 | — | — |

10. Linoleic acid methyl ester (64.4%) is heated with 1,5,7-triazabicyclo[4.4.0.]-dec-5-ene (TBD) and mesitylene under reflux (168° C.).

11.6 g of linoleic acid methyl ester(64.4%; 0.026 mol), 1.03 g of TBD (Fluka, 98%; 0.007 mol) and 11.8 g of DEGDM (0.1 mol) are charged into a flask under argon at room temperature and then heated to 168° C.

| Reaction time [h] | Linoleic acid methyl ester | CLA-ME 9c11t [Area %] | CLA-ME 10t12c [Area %] | Cis, cis- and trans, trans-CLA isomers [Area %] |
|---|---|---|---|---|
| 1 | 27.2 | 18.8 | 18.8 | 0.4 (only t, t) |
| 2 | 3.5 | 30.0 | 29.9 | 1.3 |
| 3 | 0.8 | 31.1 | 31.0 | 2.2 |
| 4 | 0.7 | 30.9 | 30.8 | 2.6 |
| 5 | 0.5 | 30.4 | 30.4 | 2.6 |
| 6 | 0 | 27.8 | 27.6 | too dilute |

We claim:

1. A process for preparing a $C_8$–$C_{24}$ alkene or alkene derivative having a conjugated double bond, which comprises isomerizing an alkene having two double bonds separated by a methylene bridge with an
   a) imino base, or
   b) iminophosphorane base,
as catalyst.

2. A process as claimed in claim 1, wherein a) is an aminoimino base and b) is an aminoiminophosphorane base.

3. A process as claimed in claim 1, wherein the alkene having two separated double bonds is a polyunsaturated fatty acid ester (FAE II), and the alkene having a conjugated double bond is a conjugated unsaturated fatty acid ester (FAE I).

4. A process as claimed in claim 3, wherein the fatty acid ester (FAE II) is an alkyl ester.

5. A process as claimed in claim 3, wherein the fatty acid ester (FAE II) is a glyceride.

6. A process as claimed in claim 5, wherein the glyceride is present in a synthetic or natural glyceride mixture.

7. A process as claimed in claim 5, wherein the glyceride mixture is of animal, microbial or vegetable origin, or a derivative or a mixture thereof.

8. A process as claimed in claim 5, wherein the glyceride is a triglyceride.

9. A process as claimed in claim 1, wherein linoleic ester is converted to conjugated linoleic ester.

10. A process as claimed in claim 1, wherein C18:2 cis-9, trans-11 and/or C18:2 trans-10, cis-12 CLAs are produced.

11. A process as claimed in claim 1, wherein the catalysis is carried out using compound (I)

$$R1-X_1\underset{R4-X_2-R3}{\overset{\phantom{X_1}}{\diagdown}}\!\!\!=\!\!N-R2 \quad (I)$$

where independently of one another $X_1$ can be —NH— or —PH—, $X_2$ can be C, N or P;

and where R1 to R4 independently of one another can be:
H,
branched or unbranched $C_1$- to $C_{20}$-alkyl, where from 0 to 3 carbon atoms can be replaced by O, S, NZ and/or —$X_3$—(C=$X_4$)—,
mono-, bi-, or tricyclic, aromatic, saturated or partially unsaturated $C_0$- to $C_6$-alkylcarbocycle or heterocycle having from 3 to 17 carbon atoms, where from 0 to 3 heteroatoms can be selected from O, S, NZ and/or —$X_3$—(C=$X_4$)—;

and where each carbon atom of the alkyl chains or of the ring can bear up to three of the following substituents OZ, SZ, (C=O)—OZ, NZZ$_1$, $C_1$- to $C_6$-alkyl;

and where $X_3$ can be a bond, O, S or NZ, and/or $X_4$ can be O, S or NZ; and where Z and/or $Z_1$ independently of one another can be H or $C_1$- to $C_6$-alkyl;

and where R1 and R4 and/or R2 and R3 can be part of a ring.

12. A process as claimed in claim 1, wherein the catalysis is carried out using compound (II)

$$(II)$$

wherein

R and R1 to R6 independently of one another can be:
H,
branched or unbranched $C_1$- to $C_{20}$-alkyl, where from 0 to 3 carbon atoms can be replaced by O, S, NZ and/or —$X_3$—(C=$X_4$)—;
mono-, bi-, or tricyclic, aromatic, saturated or partially unsaturated $C_0$- to $C_6$-alkylcarbocycle or heterocycle having from 3 to 17 carbon atoms, where from 0 to 3 heteroatoms can be selected from O, S, NZ and/or —$X_3$—(C=$X_4$)—;

and where each carbon atom of the alkyl chains or of the ring can bear up to three of the following substituents OZ, SZ, (C=O)—OZ, N$ZZ_1$, $C_1$- to $C_6$-alkyl;

where $X_3$ can be a bond, O, S or NZ, and/or $X_4$ can be O, S or NZ;

where Z and/or $Z_1$ independently of one another can be H or $C_1$- to $C_6$-alkyl;

and where different R1 to R6 can also be part of one or of different ring(s).

13. A process as claimed in claim 1, wherein the catalysis is carried out using 1,5,7-triazabicyclo[4.4.0]dec-5-ene (TBD), 1,2,3,4,4a,5,6,7-octahydro-1,8-naph-thyridine [CAS 60832-40-8], phosphazene base P4-T-BU [CAS 111324-04-0], phosphazene base P1-T-Oct No. [CAS 161118-69-0], phosphazene base P1-T-Bu-tris(tetramethylene) [CAS 161118-67-8], phosphazene base P2-T-Bu [CAS 111324-03-9], phosphazene base P4-T-Oct [CAS 153136-05-1], their salts, or the salts 1,1,1,3,3,3-hexakis (dimethylamino) diphosphazenium fluoride [CAS 137334-99-7], 1,1,1,3,3,3-hexakis(dimethylamino)diphosphazenium tetrafluoroborate [CAS 137334-98-6]or 2-tert-butylimino-2-die-thylamino-1,3-dimethylperhydro-1,3,2-diazaphosphorine [CAS 98015-45-3], or their bases.

14. A process as claimed in claim 1, wherein the catalyst is separated off.

15. A composition comprising a conjugated alkene, a fatty acid, a fatty acid ester, a glyceride, a triglyceride or mixtures thereof obtained by the process defined in claim 1, and a part or all of the catalyst employed in said process.

16. A glyceride mixture to obtained by subjecting a glyceride mixture of animal, microbial or vegetable origin and comprising at least one glyceride having two double bonds separated by a methylene bridge to the process claim 1.

17. A glyceride mixture wherein the content of conjugated fatty acids in the glyceride mixture is higher than the content of conjugated fatty acids of the starting glyceride mixture and the composition of the further glycerides essentially corresponds to the composition of a glyceride mixture as defined in claim 7.

18. An alkene, a fatty acid, a fatty acid ester, a glyceride, a triglyceride or a mixture thereof as claimed in claim 15, wherein the content of conjugated linoleic esters is at least 30% of the content of linoleic esters of the starting glyceride mixture.

19. An alkene, a fatty acid, a fatty acid ester, a glyceride, a triglyceride or a mixture thereof as claimed in claim 15, wherein the content of 11,13-octadecadienoic acid isomers, 8,10-octadecadienoic acid isomers, cis,cis-octadecadienoic acid isomers or trans/trans-octadecadienoic acid isomers is in each case less than 5% of the fatty acid content.

20. An alkene, a fatty acid, a fatty acid ester, a glyceride, a triglyceride or a mixture thereof as claimed in claim 15, wherein the CLA content in the triglyceride essentially consists of cis-9, trans-11 and trans-10, cis-12 CLA.

21. A food preparation, a food supplement preparation, an animal feed preparation, a drug preparation or a cosmetics preparation comprising the alkene, the fatty acid, the fatty acid ester, the glycerides, the triglycerides or mixtures thereof as claimed in claim 15.

22. A drug for treating allergies, diabetes, cancer, cardiovascular disorders or obesity comprising an alkene, a fatty acid, a fatty acid ester, a glyceride or a triglyceride as claimed in claim 15.

23. A process as claimed in claim 7, wherein the glyceride mixture is olive oil, canola oil, coconut oil, coconut fat, sesame seed oil, rice germ oil, bamboo oil, bamboo fat, sunflower seed oil, rapeseed oil, fish oil, tallow oil, soybean oil, palm oil, safflower oil, linseed oil, wheatgerm oil, peanut oil, cottonseed oil, corn oil, pig fat, beef fat, poultry fat, milk fat, tung oil or shea oil, or a derivative or a mixture thereof.

24. A glyceride mixture wherein the content of conjugated fatty acids in the glyceride mixture is higher than the content of conjugated fatty acids of the starting glyceride mixture and the composition of the further glycerides essentially corresponds to the composition of the glyceride mixture defined in claim 16.

25. The glyceride mixture defined in claim 16, wherein the content of conjugated linoleic esters is at least 30% of the content of linoleic esters of the starting glyceride mixture.

26. The glyceride mixture defined in claim 16, wherein the content of 11,13-octadecadienoic acid isomers, 8,10-octadecadienoic acid isomers, cis,cis-octadecadienoic acid isomers or trans/trans-octadecadienoic acid isomers is in each case less than 5% of the fatty acid content.

27. The glyceride mixture defined in claim 16, wherein the CLA content in the triglyceride essentially consists of cis-9, trans-11 and trans-10, cis-12 CLA.

28. A food preparation, a food supplement preparation, an animal feed preparation, a drug preparation or a cosmetics preparation comprising the glyceride mixture defined in claim 16.

29. A drug for treating allergies, diabetes, cancer, cardiovascular disorders or obesity comprising the glyceride mixture defined in claim 16.

* * * * *